US010119886B2

(12) United States Patent
Dhingra et al.

(10) Patent No.: US 10,119,886 B2
(45) Date of Patent: Nov. 6, 2018

(54) FILTRATION MONITORING SYSTEMS

(71) Applicant: CUMMINS FILTRATION IP, INC., Columbus, IN (US)

(72) Inventors: Amit Dhingra, Fitchburg, WI (US); Bharadwaj Prabhala, Columbus, IN (US); Abhijeet Vaidya, Columbus, IN (US); Abhijit Shimpi, Hermitage, TN (US); Eric R. Burgan, Baxter, TN (US)

(73) Assignee: CUMMINS FILTRATION IP, INC., Columbus, IN (US)

( * ) Notice: Subject to any disclaimer, the term of this patent is extended or adjusted under 35 U.S.C. 154(b) by 187 days.

(21) Appl. No.: 14/977,858

(22) Filed: Dec. 22, 2015

(65) Prior Publication Data

US 2017/0173505 A1  Jun. 22, 2017

(51) Int. Cl.
*G01M 15/04* (2006.01)
*F01M 11/03* (2006.01)
(Continued)

(52) U.S. Cl.
CPC .......... *G01M 15/042* (2013.01); *B01D 35/143* (2013.01); *F01M 11/03* (2013.01);
(Continued)

(58) Field of Classification Search
CPC .. B01D 35/143; F01M 2550/00; F01M 11/03; F01M 13/04; F01M 2013/0438;
(Continued)

(56) References Cited

U.S. PATENT DOCUMENTS 5,193,513 A * 3/1993 Marko ................ G01M 15/106
123/481
6,207,045 B1  3/2001 Jiang
(Continued)

FOREIGN PATENT DOCUMENTS

CN  101218418 A  7/2008
CN  101432741 A  5/2009
(Continued)

OTHER PUBLICATIONS

Final Office Action issued for U.S. Appl. No. 15/029,442, dated Nov. 30, 2017, 17 pages.
(Continued)

*Primary Examiner* — Manish S Shah
*Assistant Examiner* — Timothy Graves
(74) *Attorney, Agent, or Firm* — Foley & Lardner LLP

(57) ABSTRACT

A filtration monitoring system is an electronic system control module installed on an internal combustion engine or within a vehicle powered by the internal combustion engine. The filtration monitoring system monitors the health and status of the filtration systems present on the engine. The filtration monitoring system tracks filter loading patterns and predicts remaining service life of the filters by running smart algorithms based on sensor feedback (e.g., pressure sensor feedback, fluid quality characteristic sensor feedback, etc.). In some arrangements, the described filtration monitoring systems provide feedback as to whether a genuine (i.e., authorized, OEM approved, etc.) or unauthorized filter cartridge is installed in a given filtration system. The filtration monitoring system may be retrofit into an existing internal combustion engine or vehicle that does not already have a filtration monitoring system.

15 Claims, 13 Drawing Sheets

(51) Int. Cl.
  *F01M 13/04* (2006.01)
  *F02M 37/22* (2006.01)
  *G01N 15/08* (2006.01)
  *B01D 35/143* (2006.01)
  *F02M 35/02* (2006.01)
  *F02D 33/00* (2006.01)

(52) U.S. Cl.
  CPC ........... *F01M 13/04* (2013.01); *F02D 33/003* (2013.01); *F02M 35/0205* (2013.01); *F02M 37/22* (2013.01); *F02M 37/221* (2013.01); *G01N 15/08* (2013.01); *F01M 2013/0438* (2013.01); *G01N 2015/084* (2013.01)

(58) Field of Classification Search
  CPC .... F01P 11/12; F02M 37/221; G01M 15/042; G01N 15/08; G01N 2015/084
  USPC ...................................................... 73/114.31
  See application file for complete search history.

(56) References Cited

U.S. PATENT DOCUMENTS

| | | | |
|---|---|---|---|
| 6,894,489 B2 | 5/2005 | Makuuchi et al. | |
| 8,050,874 B2 | 11/2011 | Papadimitriou et al. | |
| 8,409,446 B2 | 4/2013 | Abdalla | |
| 8,673,137 B2 | 3/2014 | Verdegan et al. | |
| 9,212,627 B2 | 12/2015 | Fulton et al. | |
| 9,279,780 B2 | 3/2016 | Gwin et al. | |
| 9,345,637 B2 | 5/2016 | Larson et al. | |
| 2001/0042372 A1 | 11/2001 | Khair | |
| 2007/0061064 A1* | 3/2007 | Dollmeyer | F01N 9/002 701/114 |
| 2007/0262003 A1 | 11/2007 | Kussel | |
| 2008/0224838 A1 | 9/2008 | Rains et al. | |
| 2010/0101409 A1 | 4/2010 | Bromberg et al. | |
| 2011/0036070 A1* | 2/2011 | Schrewe | F01N 9/002 60/273 |
| 2011/0062060 A1* | 3/2011 | Royal | B01D 65/104 210/85 |
| 2011/0148584 A1 | 6/2011 | Lee et al. | |
| 2011/0153144 A1 | 6/2011 | Dlugoss et al. | |
| 2011/0259802 A1 | 10/2011 | Wieczorek et al. | |
| 2012/0083990 A1 | 4/2012 | Nevin et al. | |
| 2012/0158242 A1* | 6/2012 | Snopko | F01N 9/002 701/36 |
| 2012/0253595 A1 | 10/2012 | Oakes | |
| 2013/0036804 A1 | 2/2013 | Uehara | |
| 2013/0199983 A1 | 8/2013 | Patel et al. | |
| 2013/0220900 A1* | 8/2013 | Milvert | B01D 35/143 210/85 |
| 2013/0327696 A1 | 12/2013 | Bagci et al. | |
| 2013/0330205 A1 | 12/2013 | Apostolides et al. | |
| 2014/0123627 A1 | 5/2014 | Larose et al. | |
| 2014/0161671 A1* | 6/2014 | Cuellar | F01N 13/08 422/115 |
| 2015/0240459 A1 | 8/2015 | Kawasaki et al. | |
| 2016/0067639 A1 | 3/2016 | Shimpi et al. | |
| 2017/0080363 A1 | 3/2017 | Krause et al. | |

FOREIGN PATENT DOCUMENTS

| | | |
|---|---|---|
| WO | WO2008/074559 | 6/2008 |
| WO | WO2015/057956 A1 | 4/2015 |

OTHER PUBLICATIONS

International Search Report and Written Opinion issued for PCT/US2016/067247, dated May 5, 2017, 12 pages.
Office Action cited in U.S. Appl. No. 15/029,442, dated Apr. 5, 2018, 28 pages.

\* cited by examiner

FILTRATION MONITORING SYSTEMS

TECHNICAL FIELD

The present disclosure relates generally to filtration systems.

BACKGROUND

Internal combustion engines generally combust a mixture of fuel (e.g., gasoline, diesel, natural gas, etc.) and air. Prior to entering the engine, fluids such as fuel, oil, and air are typically passed through filter cartridges to remove contaminants (e.g., particulates, dust, water, etc.) from the fluids prior to delivery to the engine. The filter cartridges require periodic replacement as the filter media of the filter cartridges captures and removes the contaminants from the fluids passing through the filter media. In some cases, unauthorized or non-genuine replacement filter cartridges may be installed in the filtration systems during servicing operations. The unauthorized and non-genuine replacement filter cartridges may be of inferior quality to genuine, authorized filter cartridges. Thus, the use of unauthorized or non-genuine replacement filter cartridges may cause damage to the engine by allowing contaminants past the filter cartridge. Additionally, the filtration systems may have different replacement cycles, which may cause multiple service events.

SUMMARY

One example embodiment relates to an apparatus. The apparatus includes an internal combustion engine having an engine control module structured to control the operation of the internal combustion engine. The apparatus further includes a filtration system having a filter cartridge and a sensor structured to sense a characteristic associated with the filtration system. The apparatus includes a filtration monitoring system module including a processing circuit communicatively coupled to the sensor. The processing circuit includes a processor and memory. The processing circuit is structured to receive a feedback signal from the sensor relating to the characteristic, analyze the feedback signal to determine a status of the filter cartridge, calculate a percent loading of the filter cartridge, and transmit the percent loading of the filter cartridge to the engine control module.

Another example embodiment relates to a filtration monitoring system module. The module includes a circuit board having a processing circuit. The processing circuit includes a processor and memory. The processing circuit is structured to receive a feedback signal from a sensor associated with a filtration system, analyze the feedback signal to determine a status of a filter cartridge of the filtration system, and calculate a percent loading of the filter cartridge. The module further includes a housing formed around the circuit board and partially encapsulating the circuit board, the housing defining an opening. The module includes a plurality of pins extending from the circuit board and into the opening.

A further example embodiment relates to a method of installing a filtration monitoring system for an internal combustion engine. The method includes providing a filtration monitoring system module having a processing circuit structured to receive a feedback signal from a sensor associated with a filtration system associated with the internal combustion engine, analyze the feedback signal to determine a status of a filter cartridge of the filtration system, and calculate a percent loading of the filter cartridge. The method further includes connecting the filtration monitoring system module to the sensor. The method includes connecting the filtration monitoring system module to a vehicle bus such that the filtration monitoring system module can communicate data to and from an engine control module of the internal combustion engine.

These and other features, together with the organization and manner of operation thereof, will become apparent from the following detailed description when taken in conjunction with the accompanying drawings.

DETAILED DESCRIPTION

Referring to the figures generally, filtration monitoring systems are described. The filtration monitoring system is an electronic system control module installed on an internal combustion engine or within a vehicle powered by the internal combustion engine. The filtration monitoring system monitors the health and status of the filtration systems present on the engine. The filtration monitoring system tracks filter loading patterns and predicts remaining service life of the filters by running smart algorithms based on sensor feedback (e.g., pressure sensor feedback, differential pressure sensor feedback, fluid quality characteristic sensor feedback, etc.). Monitored filtration systems and fluids may include any of fuel-water separator filtration systems, fuel filtration systems, lube filtration systems, hydraulic fluid filtration systems, air filtration systems, crankcase ventilation breather systems, engine oil, coolant fluid, hydraulic fluid, air and any other filtration systems or fluids relating to the operation of the internal combustion engine or vehicle. The filtration monitoring system may be retrofit into an existing internal combustion engine or vehicle that does not already have a filtration monitoring system.

In some arrangements, the described filtration monitoring systems provide feedback as to whether a genuine (i.e., authorized, OEM approved, etc.) or unauthorized filter cartridge is installed in a given filtration system. The authorized filter determination may be based on radio frequency identification ("RFID") technology. For example, each authorized filter cartridge may be assembled with an RFID tag, which is programmed with a unique code. RFID readers with antennas in the monitored filter systems read the RFID tag information and feed any detected information into the filtration monitoring system. The filtration monitoring system analyzes the returned data (or absence thereof) to determine if a genuine (i.e., authorized, OEM approved, etc.) filter cartridge is installed or not. In some arrangements, the filtration monitoring system raises a flag if a non-authorized filter cartridge is installed.

Figure 1:
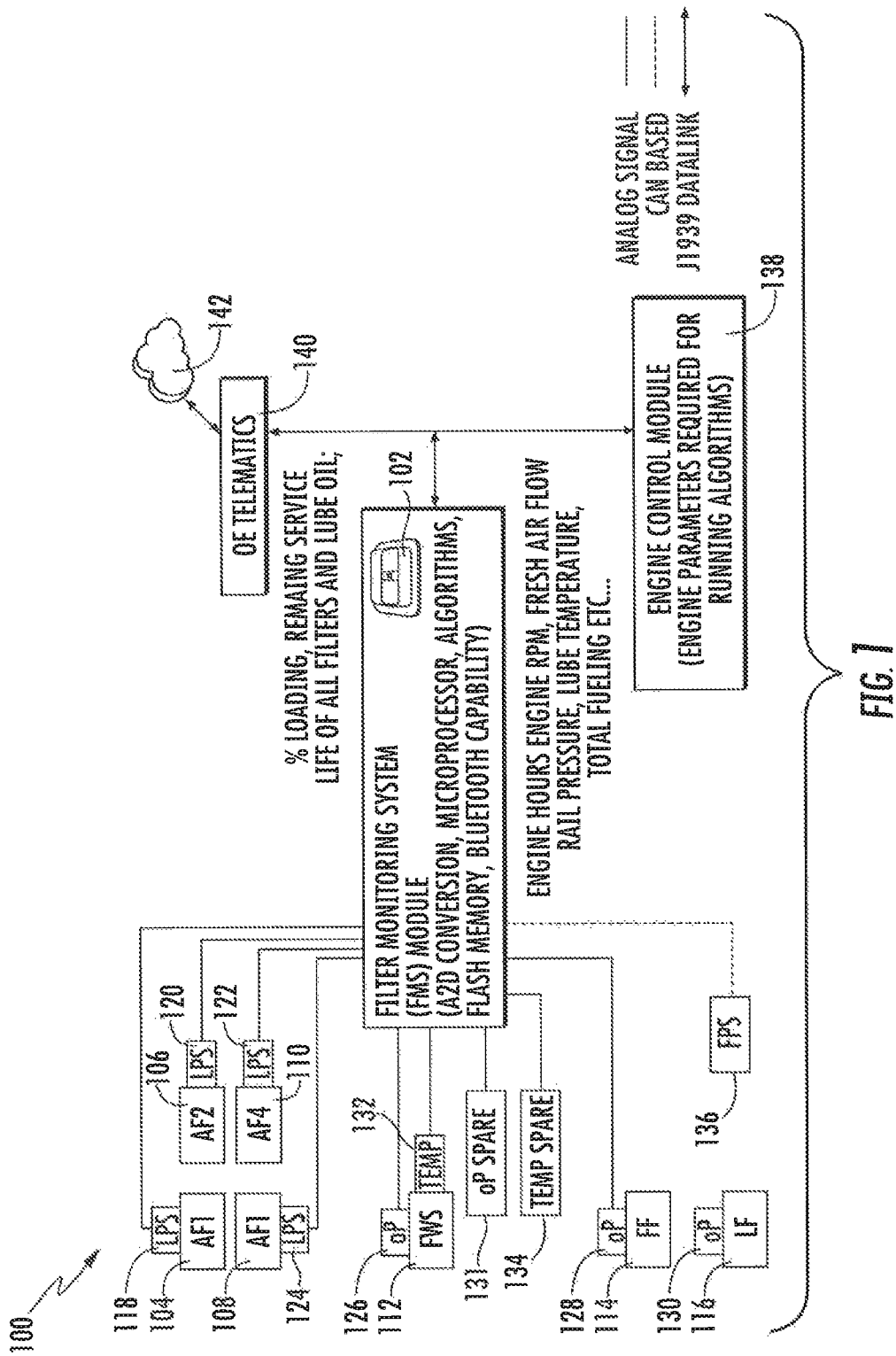
FIG. 1 is a schematic view of a filtration monitoring system according to an example embodiment.

Referring to FIG. 1, a schematic view of a filtration monitoring system 100 is shown according to an example embodiment. The filtration monitoring system 100 includes a module 102. The module 102 includes a processing circuit having a processor (e.g., a general-purpose processor, an application specific integrated circuit (ASIC), one or more field programmable gate arrays (FPGAs), a digital signal processor (DSP), a group of processing components, or other suitable electronic processing components) and memory (e.g., RAM, NVRAM, ROM, Flash Memory, hard disk storage, etc.), an analog to digital converter circuit, and various communication interfaces (e.g., analog sensor inputs, digital sensor inputs, J1939 datalink communication input/output, Bluetooth transceiver, etc.). The module 102 is structured to monitor the filtration systems of an internal combustion engine based on sensor input, engine operating parameters, and vehicle operating parameters. While various circuits with particular functionality are shown in the figures, it should be understood that the module 102 may include any number of circuits for completing the functions described herein. For example, the activities of multiple circuits may be combined as a single circuit, additional circuits with additional functionality may be included, etc. Further, it should be understood that the module 102 may further control and/or monitor other internal combustion engine systems beyond the scope of the present disclosure.

The module 102 receives sensor feedback signals from various sensors (as described in further detail below) associated with various filtration systems, the vehicle, the internal combustion engine, the ambient environment, fluid flowing through the internal combustion engine, vehicle operating parameters, or the like. In some arrangements, the sensor feedback signals relate to a sensed characteristic of an associated filtration system. The sensors may include any of pressure sensors, pressure drop sensors, pressure differential sensors, fluid characteristic sensors, moisture sensors, temperature sensors, fluid flow sensors, or the like. The sensors provide input into the module 102 such that the module can determine the pressure differential across a given filtration system thereby determining the loading of the installed filter cartridge. In the particular arrangement of FIG. 1, the module receives feedback from sensors associated with four different air filtration systems 104, 106, 108, and 110 ("AF#"), a fuel-water separator filtration system 112 ("FWS"), a fuel filtration system 114 ("FF"), and a lubricant filtration system 116 ("LF"). However, it should be understood that any combination of filtration systems may provide feedback to the module 102. For example, in some arrangements, the module 102 may receive feedback from sensors associated with a crankcase ventilation breather system.

As shown in FIG. 1, the module 102 receives feedback signals from four low pressure sensors 118, 120, 122, and 124 ("LPS") each associated with one of the air filtration systems 104, 106, 108, and 110. Each of the low pressure sensors 118, 120, 122, and 124 provides feedback to the module indicating a loading of a filter cartridge of a respective one of the air filtration systems 104, 106, 108, and 110. The module 102 receives feedback signals from four pressure differential sensors 126, 128, 130, and 131 ("dP"): a pressure differential sensor 126 associated with stage one of the fuel-water separator filtration system 112, a pressure differential sensor 128 associated with stage two of the fuel filtration system 114, a pressure differential sensor 130 associated with the lubricant filtration system 116, and a spare pressure differential sensor 131. The pressure differential sensors 126, 128, and 130 are associated with a specific filtration system and provide feedback to the module 102 indicating a loading of a filter cartridge associated with the respective filtration system. The spare pressure differential sensor 131 can provide feedback to the module 102 for a later installed system or for a non-filtration pressure feedback (e.g., an ambient environment pressure reading). The module 102 receives feedback signals from two temperature sensors ("temp"): a first temperature sensor 132 to monitor the inlet fuel temperature into the fuel-water separator filtration system 112 and a second temperature sensor 134 that can provide the temperature for a later installed system or a non-filtration temperature (e.g., an ambient environment temperature). Additionally, the module 102 receives feedback signals from a fluid property sensor 136. The fluid property sensor 136 may be configured to monitor a characteristic of a fluid (e.g., oil, lubricant, air, fuel, hydraulic fluid, etc.) entering the internal combustion engine.

The module 102 includes ten analog input channels. Accordingly, each of the sensors 118 through 134 communicates with the module 102 via an analog signal line. In some arrangements, a sensor feedback signal is an analog signal and the module 102 converts the analog signal from a given sensor into a digital signal via the analog to digital converter circuit before analyzing the given signal. The module 102 further includes a controller area network ("CAN") input. The CAN input is a digital input. The fluid property sensor 136 provides feedback to the module 102 via the CAN input.

Still referring to FIG. 1, the module 102 communicates data to and from an engine control module 138 via a digital datalink. The engine control module 138 generally controls the operation of the internal combustion engine. In some arrangements, the digital datalink is a J1939 vehicle bus datalink. Through the digital datalink, the module 102 can receive internal combustion engine and vehicle operating parameters needed for various filter life calculations. In some arrangements, the engine control module 138 provides the module 102 with real-time operating parameters indicating the number of hours the engine has been run, the current engine RPM, the fresh air flow rate into the air intake system, the fuel rail injector pressure, the lubricant oil temperature, the total amount of fuel input into the internal combustion engine, the age of the lubricant oil, and the like. Additionally, the module 102 can provide filtration system status information to the engine control module 138 via the digital datalink. For example, the module 102 can send status messages to the engine control module 138 indicating the status of the various filtration systems. In some arrangements, the status messages relate to clear or normal or good statuses indicating that the associated filtration system is operating normally. In other arrangements, the status messages relate to error or service conditions indicating the associated filtration system requires service. In such arrangements, the engine control module 138 can present a warning to the operator of the internal combustion engine or vehicle (e.g., a dashboard light, an audible alert, an alert through an original equipment telematics box, etc.).

The module 102 also communicates data to and from other devices, such as an original equipment ("OE") telematics box 140 or external devices (e.g., an operator device, a technician device, a cloud storage system via the external network 142, etc.). For example, the module 102 can communicate status information, such as percent loading of a filter cartridge, remaining service life of a filter cartridge, fluid characteristics, and the like, to the telematics box 140 for sending to a remote server (e.g., via an external network 142) or to external devices. In some arrangements, the communication of data to and from the external devices occurs over the digital datalink. In other arrangements, the communication of data to and from the external devices occurs via a wireless data protocol, such as a Bluetooth, a WiFi, and/or a cellular communication link. In additional arrangements, the data exchange with the external devices occurs via the engine control module 138.

Figure 2:
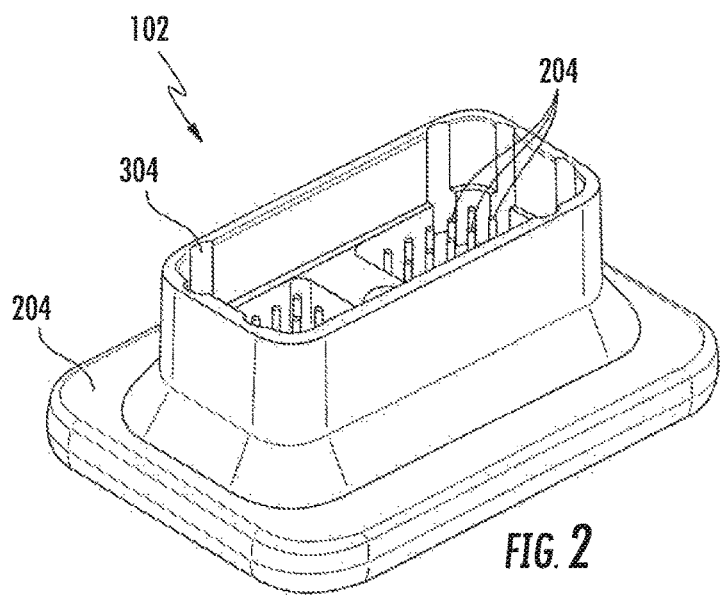
FIG. 2 is a perspective view of a module of the filtration monitoring system of FIG. 1.
Figure 3:
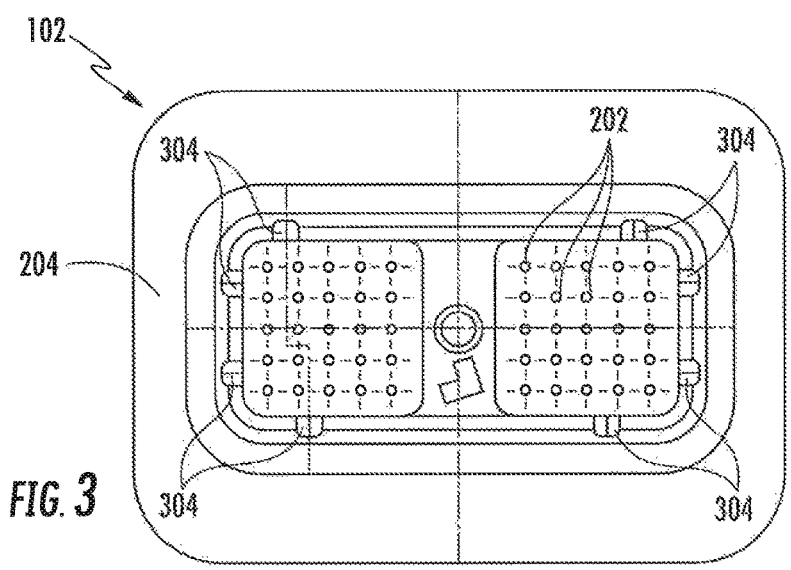
FIG. 3 is a top view of the module of the filtration monitoring system of FIG. 1.
Figure 4:
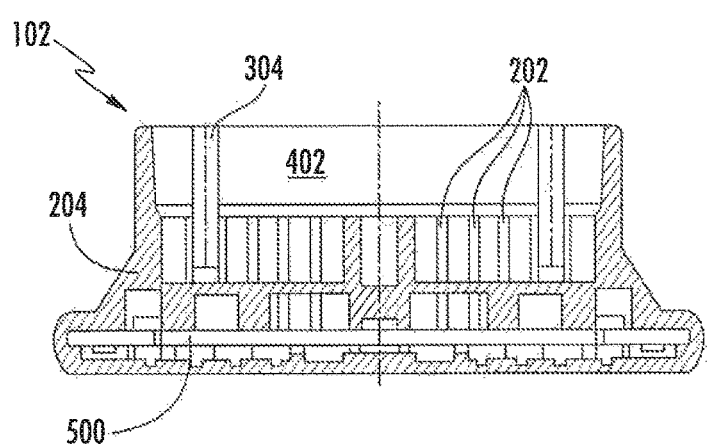
FIG. 4 is a cross-sectional view of the module of the filtration monitoring system of FIG. 1.
Figure 5:
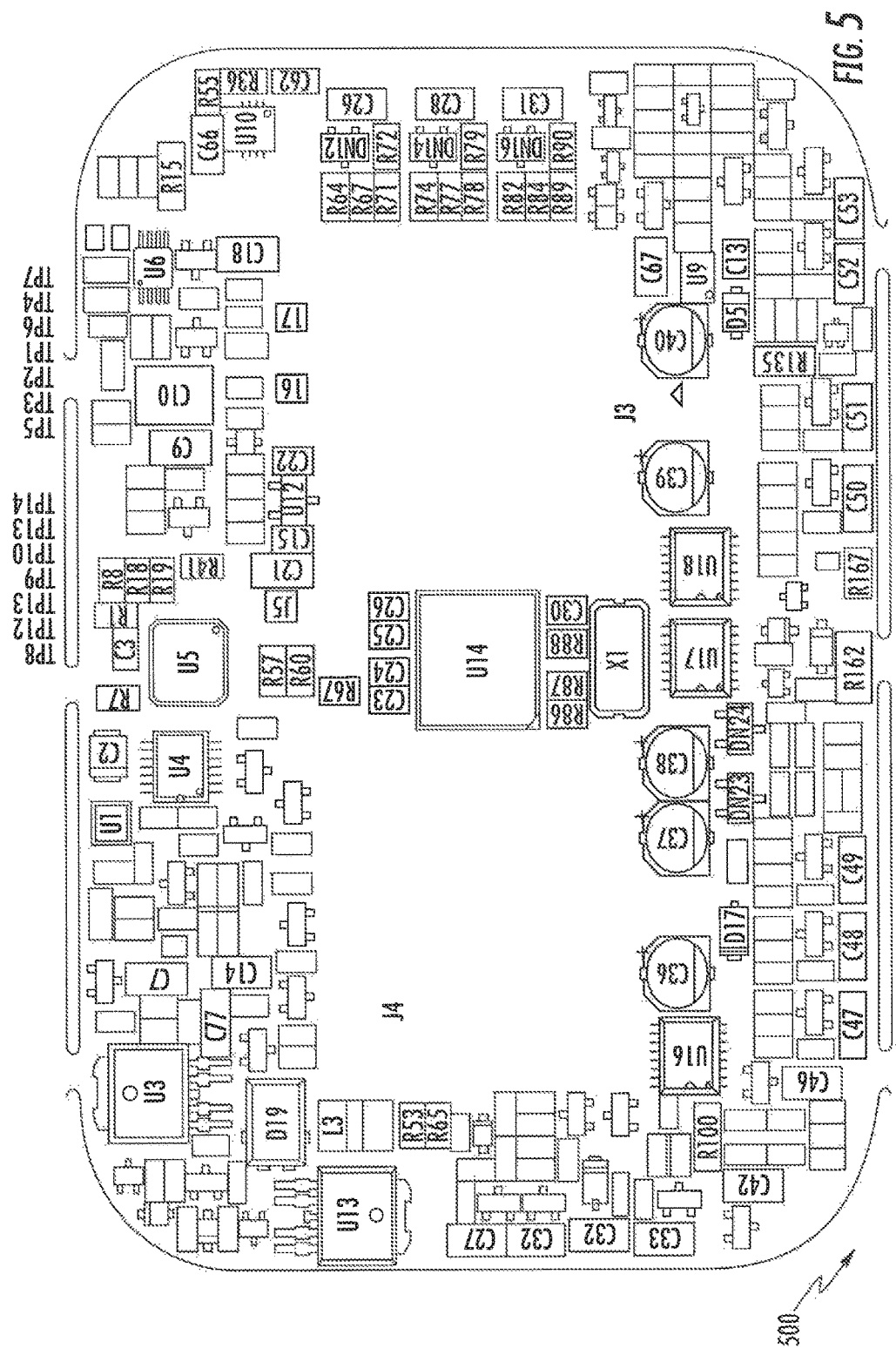
FIG. 5 is a schematic view of the circuit board of the module of the filtration monitoring system of FIG. 1.
Figure 6:
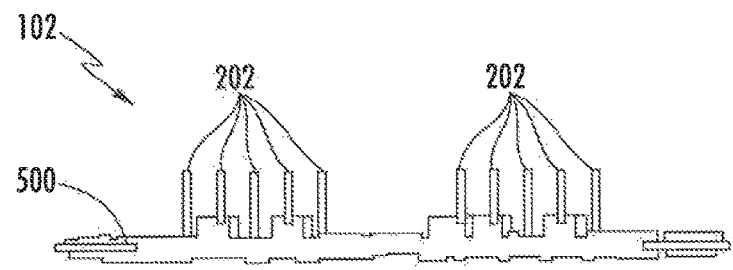
FIG. 6 is a side perspective view of a pin arrangement of the module of the filtration monitoring system of FIG. 1.

Various views of the module 102 and its components are shown in FIGS. 2 through 6. FIG. 2 shows a perspective view of the module 102. FIG. 3 shows a top view of the module 102. FIG. 4 shows a cross-sectional view of the module 102. FIG. 5 shows a schematic view of the circuit board 500 of the module 102. FIG. 6 shows a side perspective view of the pin arrangement of the module 102. The module 102 is packaged in the configuration as shown in FIGS. 1 through 3. Generally, the module includes a circuit board 500 having a plurality of pins 202 extending from the circuit board 500. The pins 202 provide electrical contacts for the various inputs and outputs of the module 102. In some arrangements, the module 102 includes fifty pins 202 arranged in two twenty-five pin arrays (e.g., as shown best in FIG. 3) such that the module 102 can be connected to a standard Deutsch or Delphi data connector (e.g., connector 700 as discussed below with respect to FIG. 7). The twenty-five pin arrays are each five by five arrays. It should be noted, however, that the module 102 can include any other number of pins arranged in any geometric manner. For example, and as described in further detail below with respect to FIGS. 17 through 25, a module 1702 can include twenty-four pins.

The module 102 includes a housing 204. The housing 204 is formed around the circuit board 500 having the processing circuit and the pins 202 by an injection molding process in which the circuit board 500 assembled with all electronic components (e.g., as shown in FIG. 5) is fed into an injection mold machine via an insert into the mold tool cavity. Melted molding material in pressurized form (e.g., Hysol MG33F, plastic, or another type of epoxy molding compound designed for encapsulation of electronic components) is poured around the circuit board and cured to form the shape of the housing 102. The housing 102 partially encapsulates the circuit board 500. In some arrangements, the pins 202 are assembled onto the module 102 after molding of the housing 102 around the circuit board 500 is complete. The pins 202 from the circuit board 500 into an opening 402 defined in a wall of the housing 102 such that the pins 202 are exposed for a connector. In some arrangements, the housing 204 includes an alignment tab 302 and alignment slots 304. The alignment tab 302 ensures that the module 102 can only be installed on the appropriate connector in a single orientation.

Figure 7:
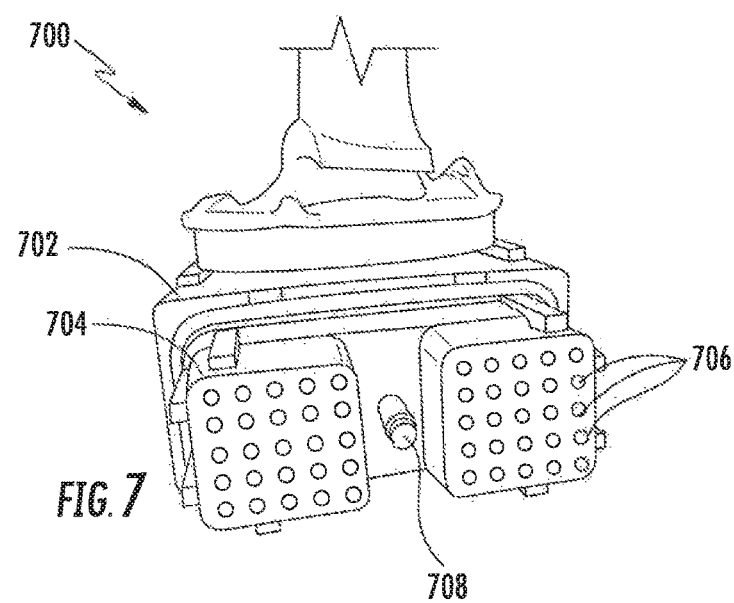
FIG. 7 is a perspective view of a connector according to an example embodiment.

Referring to FIG. 7, a perspective view of a connector 700 is shown according to an example embodiment. The connector 700 is configured to connect the various components (e.g., the sensors, the engine control module 138, etc.) to the module 102. The connector includes a housing 702 having an extension 704. The extension 704 includes a plurality of pin connectors 706. The pin connectors 706 are arranged to align with the pins 202 when the extension 704 is received in the opening 402 of the module 102. Accordingly, in some arrangements, the connector 700 includes fifty pin connectors 706 arranged in two twenty-five pin arrays. In some arrangements, the connector 700 is a Deutsch or Delphi standard connector. In some arrangements, the connector 700 includes a screw 708 that is configured to secure the connector 700 to the module 102.

Figure 8:
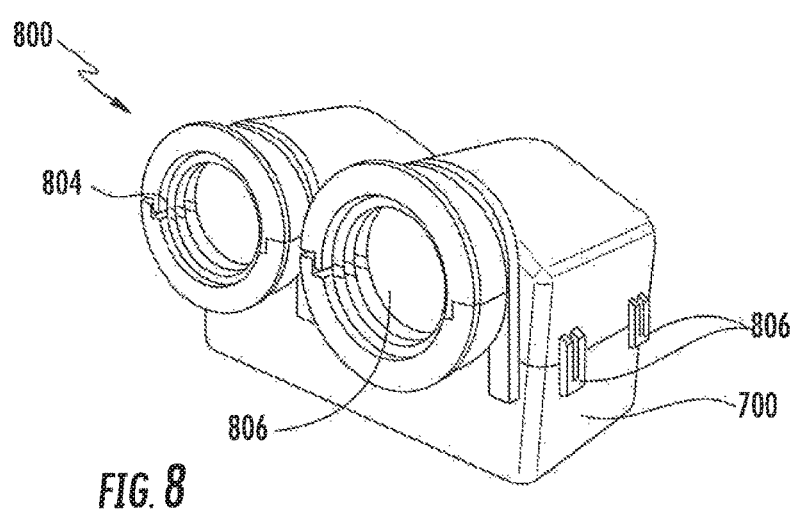
FIG. 8 is a backshell is shown according to an example embodiment.

Referring to FIG. 8, a backshell 800 is shown according to an example embodiment. The backshell 800 connects to the connector 700 via snap-fit connectors 802. The backshell 800 covers a portion of the connector 700 and provides wire routing openings 804 and 806. The wire routing openings 804 and 806 protect the connections between the wires providing the various inputs and outputs to and from the module and the connector 700.

The module 102 generally monitors the filtration systems of an internal combustion engine based on sensor input, engine operating parameters, and vehicle operating parameters. To do so, the module 102 receives feedback signals from the various sensors related to the sensed characteristics of the various filtration systems and engine operating parameters from the engine control module 138. The module 102 analyzes the received information (e.g., sensor feedback signals, engine operating parameters, etc.) through filtration system specific algorithms loaded in the processor of the module 102. Different sets of algorithms for each filtration system run in parallel during operation of the module 102. For each filtration system, the module 102 determines a status of a filter cartridge installed in the filtration system. In some arrangements, the status of the filter cartridge relates to the percent loading of the filter cartridge and remaining service life of the filter cartridge. In some arrangements, the module 102 also determines current quality of the oil through an oil quality algorithm to provide information on how the oil will last before needing replacement. The output of the module 102 (i.e., the percent loading of each filter cartridge, the remaining service life of each filter cartridge, the oil quality, the time to replacement for the oil, etc.) is transmitted to the engine control module 138.

In some arrangements, the output of the module 102 is integrated with the original equipment (OE) telematics box/ system 140 the digital datalink (e.g., via a J-1939 datalink protocol). This integration provides real-time or batch information concerning each filtration system of the internal combustion engine. This information assists technicians, fleet managers, vehicle operators, and the like in making real-time service decisions with respect to the various filtration systems and the vehicle's operation. In some arrangements, the output of the module is received on a mobile device via the Bluetooth transceiver of the module 102 (e.g., a BTLE 4.0 transceiver) such that the data is viewable a mobile device application (e.g., a smartphone application).

In certain arrangements, the module 102 includes extended flash memory. The extended flash memory enables the module 102 to capture and store historic use and filtration system status information (e.g., percent loading, remaining service life, etc.) for each of the filtration systems monitored and for any fluids monitored (e.g., lube oil). The stored historic use and status information may be stored at every key-off/key-on event for the internal combustion engine. Accordingly, the module 102 can function as a data recorder that can be used to analyze operating parameters of the internal combustion engine and the monitored filtration systems if needed for the process of troubleshooting any filter or engine system failures (e.g., while examining a warranty claim or investigating an engine failure).

Figure 9:
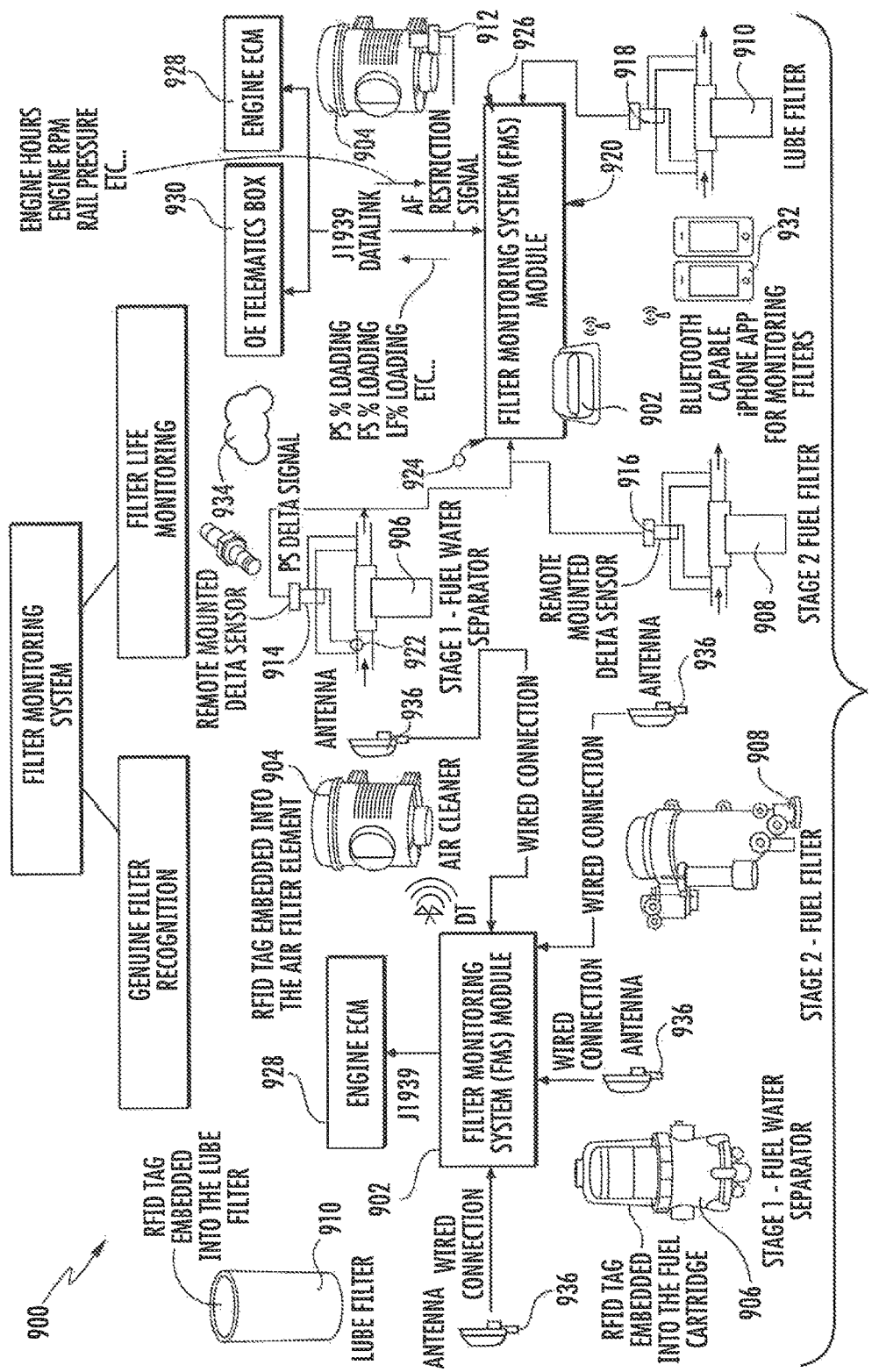
FIG. 9 is a schematic view of a filtration monitoring system according to another example embodiment.

Referring to FIG. 9, a schematic view of a filtration monitoring system 900 is shown according to an example embodiment. The filtration monitoring system 900 is similar to the filtration monitoring system 100 described above with respect to FIGS. 1 through 8. The primary difference between the filter monitoring system 900 and the filter monitoring system 100 is that the filter monitoring system 900 performs genuine filter recognition and filter life monitoring functions, whereas the filter monitoring system 100 does not perform genuine filter recognition. The filtration monitoring system 900 includes a module 902. The module 902 includes a processing circuit having a processor (e.g., a general-purpose processor, an application specific integrated circuit (ASIC), one or more field programmable gate arrays (FPGAs), a digital signal processor (DSP), a group of processing components, or other suitable electronic processing components) and memory (e.g., RAM, NVRAM, ROM, Flash Memory, hard disk storage, etc.), an analog to digital converter circuit, and various communication interfaces (e.g., analog sensor inputs, digital sensor inputs, coaxial RFID antenna inputs, J1939 datalink communication input/output, Bluetooth transceiver, etc.). The module 902 generally monitors the filtration systems of an internal combustion engine based on sensor input, engine operating parameters, and vehicle operating parameters. Additionally, the module 902 verifies installed filter cartridges as being genuine (i.e., authentic or OEM approved) based on a filter ID stored in an RFID tag of a given filter cartridge. While various circuits with particular functionality are shown in the figures, it should be understood that the module 902 may include any number of circuits for completing the functions described herein. For example, the activities of multiple circuits may be combined as a single circuit, additional circuits with additional functionality may be included, etc. Further, it should be understood that the module 902 may further control and/or monitor other internal combustion engine systems beyond the scope of the present disclosure.

The module 902 receives feedback signals from various sensors associated with various filtration systems, the vehicle, the internal combustion engine, the ambient environment, fluid flowing through the internal combustion engine, vehicle operating parameters, or the like. The sensors may include any of pressure sensors, pressure drop sensors, fluid characteristic sensors, moisture sensors, temperature sensors, fluid flow sensors, or the like. The sensors provide input into the module 902 such that the module can determine the pressure differential across a given filtration system thereby determining the loading of the installed filter cartridge. In the particular arrangement of FIG. 9, the module receives feedback from sensors associated with an air filtration systems 904, a fuel-water separator filtration system 906, a fuel filtration system 908, and a lubricant filtration system 910. However, it should be understood that any combination of filtration systems may provide feedback to the module 902. For example, in some arrangements, the module 902 may receive feedback from sensors associated with a crankcase ventilation breather system.

As shown in FIG. 9, the module 902 receives feedback signals from a low pressure sensor 912 associated with the air filtration system 904. The low pressure sensor 912 provides feedback to the module 902 indicating a loading of a filter cartridge of the air filtration system 904. The module 902 receives feedback signals from four pressure differential sensors ("dP"): a pressure differential sensor 914 associated with stage one of the fuel-water separator filtration system 906, a pressure differential sensor 916 associated with stage two of the fuel filtration system 908, a pressure differential sensor 918 associated with the lubricant filtration system 910, and a spare pressure differential sensor 920. The pressure differential sensors 914, 916, and 918 are associated with a specific filtration system and provide feedback to the module 902 indicating a loading of a filter cartridge associated with the respective filtration system. The spare pressure differential sensor 920 can provide feedback to the module 902 for a later installed system or for a non-filtration pressure feedback (e.g., an ambient environment pressure reading). The module 902 receives feedback signals from two temperature sensors: a first temperature sensor 922 to monitor the inlet fuel temperature into the fuel-water separator filtration system 906 and a second temperature sensor 924 that can provide the temperature for a later installed system or a non-filtration temperature (e.g., an ambient environment temperature). Additionally, the module 102 receives feedback signals from a fluid property sensor 926. The fluid property sensor 926 may be configured to monitor a characteristic of a fluid (e.g., oil, lubricant, air, fuel, hydraulic fluid, etc.) entering the internal combustion engine.

The module 902 includes seven analog input channels. Accordingly, each of the sensors communicates with the module 902 via an analog signal line. In some arrangements, the module 902 converts the input analog signal from a given sensor into a digital signal before analyzing the given signal. The module 902 further includes a controller area network ("CAN") input. The CAN input is a digital input. The fluid property sensor 926 provides feedback to the module 902 via the CAN input.

Still referring to FIG. 9, the module 902 communicates data to and from an engine control module 928 via a digital datalink. The engine control module 928 generally controls the operation of the internal combustion engine. In some arrangements, the digital datalink is a J1939 vehicle bus datalink. Through the digital datalink, the module 902 can receive internal combustion engine and vehicle operating parameters needed for various filter life calculations. In some arrangements, the engine control module 928 provides the module 902 with real-time operating parameters indicating the number of hours the engine has been run, the current engine RPM, the fresh air flow rate into the air intake system, the fuel rail injector pressure, the lubricant oil temperature, the total amount of fuel input into the internal combustion engine, the age of the lubricant oil, and the like. Additionally, the module 902 can provide filtration system status information to the engine control module 928 via the digital datalink. For example, the module 902 can send status messages to the engine control module 928 indicating the status of the various filtration systems. In some arrangements, the status messages relate to clear or normal or good statuses indicating that the associated filtration system is operating normally. In other arrangements, the status messages relate to error or service conditions indicating the associated filtration system requires service. In such arrangements, the engine control module 928 can present a warning to the operator of the internal combustion engine or vehicle (e.g., a dashboard light, an audible alert, etc.).

The module 902 also communicates data to and from other devices, such as an original equipment ("OE") telematics box 930, a mobile device 932 associated with an operator or a technician (e.g., via a Bluetooth or WiFi connection), or external devices (e.g., a cloud storage system via the external network 934). For example, the module 902 can communicate status information, such as percent loading of a filter cartridge, remaining service life of a filter cartridge, fluid characteristics, and the like, to the telematics box 930 for sending to a remote server (e.g., via an external network 934) or to external devices. In some arrangements, the communication of data to and from the external devices occurs over the digital datalink. In other arrangements, the communication of data to and from the external devices occurs via a wireless data protocol, such as a Bluetooth, a WiFi, and/or a cellular communication link. In additional arrangements, the data exchange with the external devices occurs via the engine control module 928.

In addition to filtration system monitoring, the module 902 is structured to determine whether genuine filter cartridges are installed in the various filtration systems of the internal combustion engine. The module 902 receives data from RFID antennas 936. Each monitored filtration system has an associated one of the RFID antennas 936 communicatively coupled to the module 902. In the arrangement of FIG. 9, the system 900 has four RFID antennas 936: one associated with the air filtration systems 904, one associated with the fuel-water separator filtration system 906, one associated with the fuel filtration system 908, and one associated with the lubricant filtration system 910. When a filter cartridge is installed in any of the filtration systems, the associated RFID antenna is structured to interrogate and gather data (e.g., a serial number, a filter identifier, a filter manufacturing date, etc.) from an RFID tag installed on the filter cartridge (if the filter cartridge has an RFID tag) and to send the data to the module 902. The module 902 determines whether the installed filter cartridge is genuine based on analyzing returned data (or absence thereof) and comparing the returned data to expected data. If no data or unexpected data is received from the installed filter cartridge, the module 902 determines that no filter or an unauthorized filter is installed in the filtration system. In some arrangements, the module 902 initiates an alert to indicate the unauthorized or absent filter cartridge. In some arrangements, the module 902 sends a message to the engine control module 928 to initiate an alert to the operator (i.e., a dashboard light, an audible alarm). In other arrangements, the module 902 initiates an alert message to the mobile device 932 via the Bluetooth or WiFi connection. In further arrangements, the module 902 initiates an alert to the OE telematics box 930 for sending to the remote server. If expected data is returned from an RFID tag of the installed filter cartridge, the module 902 indicates that the filtration system is operating as expected.

As discussed above, genuine filtration cartridges include an RFID tag readable by the RFID antennas 936. In some arrangements, the RFID tag stores a unique identifier code. The unique identifier code is stored in memory of the RFID tag. In some arrangements, the unique identifier code is a proprietary code generated in accordance with an algorithm set by the manufacturer of a genuine filtration cartridge that can be decoded by the module 902.

Figure 10:
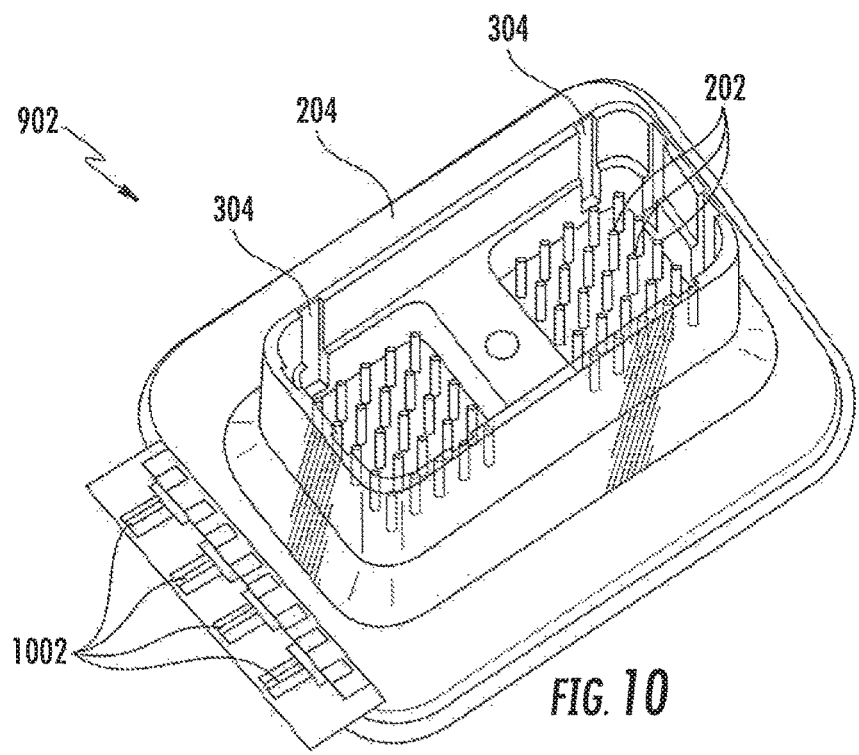
FIG. 10 is a perspective view of the module of the filtration monitoring system of FIG. 9.
Figure 11:
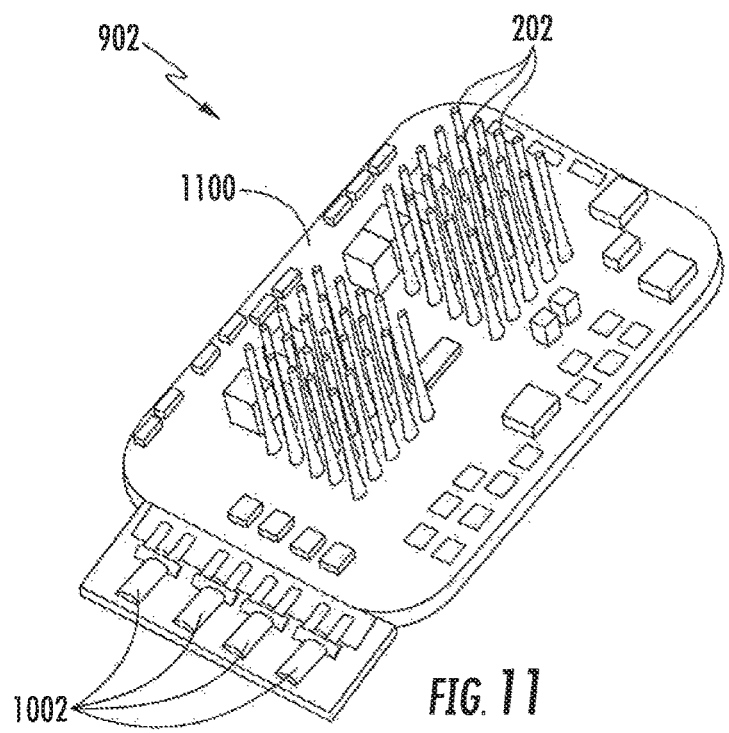
FIG. 11 is a perspective view of a circuit board of the module of FIG. 10.

Views of the module 902 and its components are shown in FIGS. 10 and 11. FIG. 10 shows a perspective view of the module 902. FIG. 11 shows a perspective view of a circuit board 1100 of the module 902. The module 902 is arranged in a substantially the same manner as the module 102. Accordingly, the same numbering is used between module 902 and 102 to designate similar parts. The primary difference between the module 902 and the module 102 is the inclusion of four coaxial connectors 1002 in the module 902. The four coaxial connectors 1002 provide input for the four RFID antennas 936. Although shown as extending from a side of the module 902, the coaxial connectors 1002 can be arranged in any position around the module 902. Additionally, the circuit board 1100 of the module 902 has a different arrangement of components than the circuit board 500 to account for the different inputs of the module 902. Other than the two noted differences, the module 902 and the module 102 are arranged and manufactured in the same manner. Accordingly, the module 902 can be connected to the connector 700 and the backshell 800 in the same manner as described above with respect to the module 102.

In addition to performing the genuine filter analysis, the module 902 generally monitors the filtration systems of an internal combustion engine based on sensor input, engine operating parameters, and vehicle operating parameters. To do so, the module 902 analyzes the received information (e.g., sensor feedback signals, engine operating parameters, etc.) through filtration system specific algorithms loaded in the processor of the module 902. Different sets of algorithms for each filtration system run in parallel during operation of the module 902. For each filtration system, the module 902 determines the percent loading of the filter cartridge and remaining service life of the filter cartridge. In some arrangements, the module 902 also determines current quality of the oil through an oil quality algorithm to provide information on how the oil will last before needing replacement. The output of the module 902 (i.e., the percent loading of each filter cartridge, the remaining service life of each filter cartridge, the oil quality, the time to replacement for the oil, etc.) is provided to the engine control module 928.

In some arrangements, the output of the module 902 is integrated with the OE telematics box 930 through the digital datalink (e.g., via a J-1939 datalink protocol). This integration provides real-time or batch information concerning each filtration system of the internal combustion engine. This information assists technicians, fleet managers, vehicle operators, and the like in making real-time service decisions with respect to the various filtration systems and the vehicle's operation. In some arrangements, the output of the module is received on a mobile device via the Bluetooth transceiver of the module 902 (e.g., a BTLE 4.0 transceiver) such that the data is viewable a mobile device application (e.g., a smartphone application).

In certain arrangements, the module 902 includes extended flash memory. The extended flash memory enables the module 902 to capture and store historic use and filtration system status information (e.g., percent loading, remaining service life, etc.) for each of the filtration systems monitored and for any fluids monitored (e.g., lube oil). The stored historic use and status information may be stored at every key-off/key-on event for the internal combustion engine. Accordingly, the module 902 can function as a data recorder that can be used to analyze operating parameters of the internal combustion engine and the monitored filtration systems if needed for the process of troubleshooting any filter or engine system failures (e.g., while examining a warranty claim or investigating an engine failure).

Figure 12:
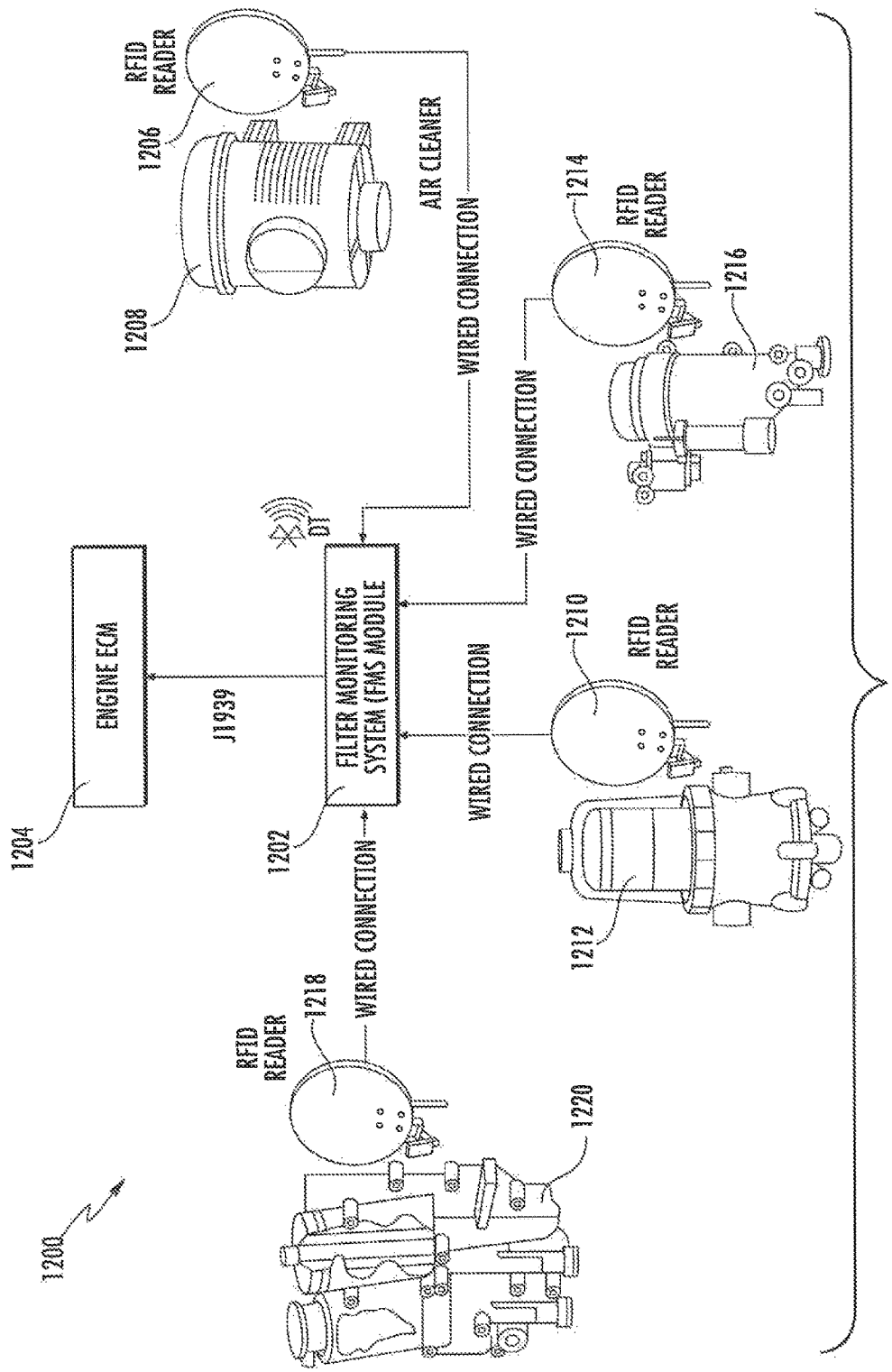
FIG. 12 is a schematic view of a filtration monitoring system of an internal combustion engine according to a further example embodiment.

Referring to FIG. 12, a schematic view of a filtration monitoring system 1200 of an internal combustion engine is shown according to an example embodiment. The filtration monitoring system 1200 is similar to the filtration monitoring system 900 described above with respect to FIGS. 9 through 11. The primary difference between the filtration monitoring system 1200 and the filter monitoring system 900 is that the filtration monitoring system 1200 only performs genuine filter recognition and does not perform filter life monitoring functions, whereas the filter monitoring system 900 performs both of these features. The filtration monitoring system 1200 includes a module 1202. As described in further detail below, the module 1202 verifies installed filter cartridges as being genuine (i.e., authentic or OEM approved) based on a filter ID stored in an RFID tag of a given filter cartridge.

Figure 13:
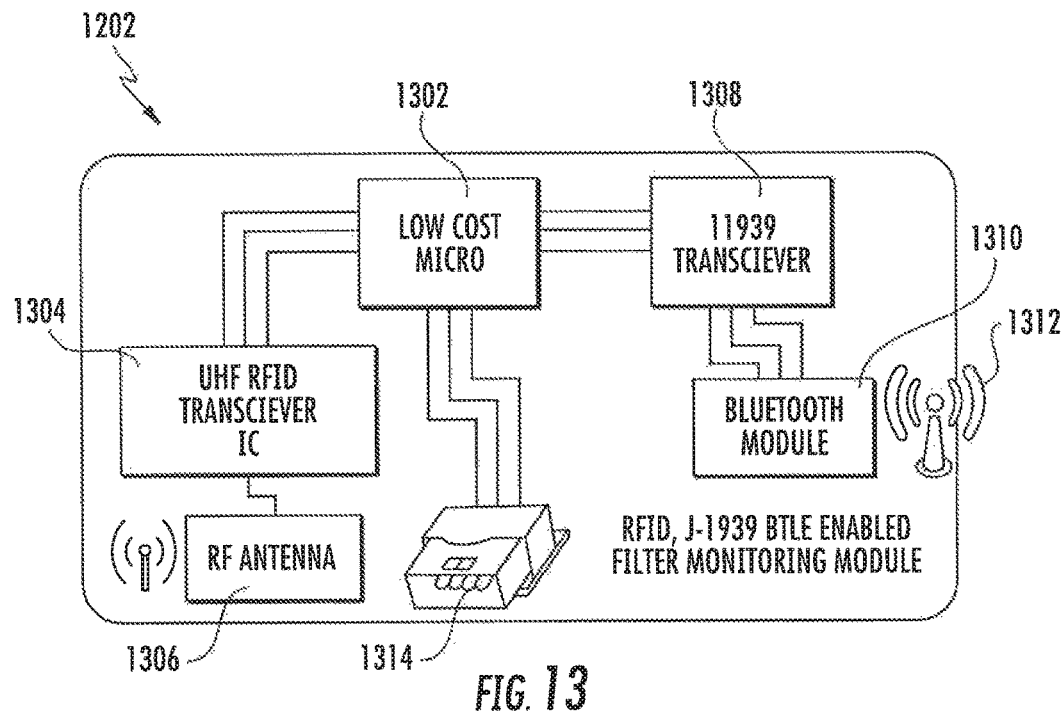
FIG. 13 is a diagram of a module of the filtration monitoring system of FIG. 12.

A diagram of the module 1202 is shown in FIG. 13. As shown in FIG. 13, the module 1202 includes a processing circuit having a processor 1302 (e.g., a general-purpose processor, an application specific integrated circuit (ASIC), one or more field programmable gate arrays (FPGAs), a digital signal processor (DSP), a group of processing components, or other suitable electronic processing components) and memory (e.g., RAM, NVRAM, ROM, Flash Memory, hard disk storage, etc.). In some arrangements, the processor 1302 includes the memory. The processor 1302 further includes an RFID transceiver 1304. In some arrangements, the RFID transceiver 1304 is an ultra-high frequency ("UHF") RFID transceiver. The RFID transceiver 1304 is communicatively coupled to the processor 1302. The RFID transceiver 1304 is communicatively coupled to a RFID antenna 1306. As described in further detail below, the module 1202 uses the RFID transceiver 1304 and the RFID antenna 1306 to interrogate RFID chips embedded in filtration cartridges installed in a monitored filtration system to determine if the installed filtration cartridge is genuine (i.e., authorized, OEM approved, etc.). Although shown as being within the module 1202, the RFID antenna 1306 can be positioned outside of and remote from the module 1202 such that the RFID antenna 1306 is electrically coupled to the module 1202 via a wire (e.g., a coaxial wire). In some arrangements, the module 1202 is coupled to multiple RFID antennas (e.g., as shown in FIG. 12 and as discussed in further detail below). The module 1202 includes a J1939 transceiver 1308. The J1939 transceiver sends and receives data to and from the engine control module 1204 (as shown in FIG. 12). In some arrangements, the module 1202 includes a Bluetooth transceiver 1310 (e.g., a BTLE 4.0 transceiver) that allows the module 1202 to communicate with external devices (e.g., a smartphone associated with an operator or a technician). In such arrangements, the module 1202 may have an integrated or an external Bluetooth antenna 1312. In other arrangements, the module 1202 does not include a Bluetooth transceiver. The module 1202 also includes a connector 1314. The connector 1314 connects the module 1202 to the J1939 vehicle bus and provides operating power to the module 1202. The module 1202 is covered by an enclosure (e.g., in a similar manner as described above with respect to the module 102 and the module 902) for robustness and durability purposes.

Figure 14:
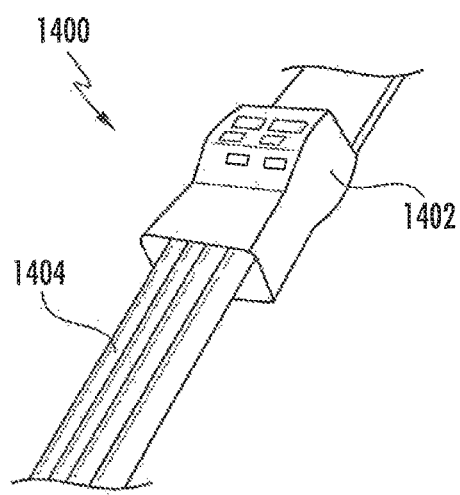
FIG. 14 is a perspective view of a connector according to another example embodiment.

Referring to FIG. 14, a perspective view of a connector 1400 is shown according to an example embodiment. The connector 1400 is removably connectable to the connector 1314. The connector 1400 includes a male connection portion 1402 and a wiring harness 1404. The male connection portion 1402 can be inserted into the connector 1314 of the module 1202 to electrically connect the module 1202 to the J1939 vehicle bus such that the module 1202 can communicate with the engine control module 1204 and receive operational power. In some arrangements, the connector 1400 is a four pin connector.

Referring again to FIG. 12, in the filtration monitoring system 1200, the module receives input from four RFID antennas: a first RFID antenna 1206 associated with an air filtration system 1208, a second RFID antenna 1210 associated with a fuel-water separator filtration system 1212, a third RFID antenna 1214 associated with a fuel filtration system 1216, and a fourth RFID antenna 1218 associated with a lubricant filtration system 1220. Although four filtration systems are shown, it should be understood that any number of filtration systems can be monitored with an associated RFID antenna.

The module 1202 determines whether genuine filter cartridges are installed in the various filtration systems of the internal combustion engine. The module 1202 receives data from the RFID antennas associated with the filtration systems. Each monitored filtration system has an associated one of the RFID antennas. When a filter cartridge is installed in any of the filtration systems, the associated RFID antenna will interrogate and gather data (e.g., a serial number, a filter identifier, a filter manufacturing date, a unique identifier code as discussed above with respect to the module 902, etc.) from an RFID tag installed on the filter cartridge (if the filter cartridge has an RFID tag). The module 1202 determines whether the installed filter cartridge is genuine based on analyzing returned data (or absence thereof) and comparing the returned data to expected data. If no data or unexpected data is received from the installed filter cartridge, the module 1202 determines that no filter or an unauthorized filter is installed in the filtration system. In some arrangements, the module 1202 initiates an alert to indicate the unauthorized or absent filter cartridge. In some arrangements, the module 1202 sends a message to the engine control module 1204 to initiate an alert to the operator (i.e., a dashboard light, an audible alarm). In other arrangements, the module 1202 initiates an alert message to a mobile device via the Bluetooth transceiver 1310. If expected data is returned from an RFID tag of the installed filter, the module 1202 indicates that the filtration system is operating as expected.

Figure 15:
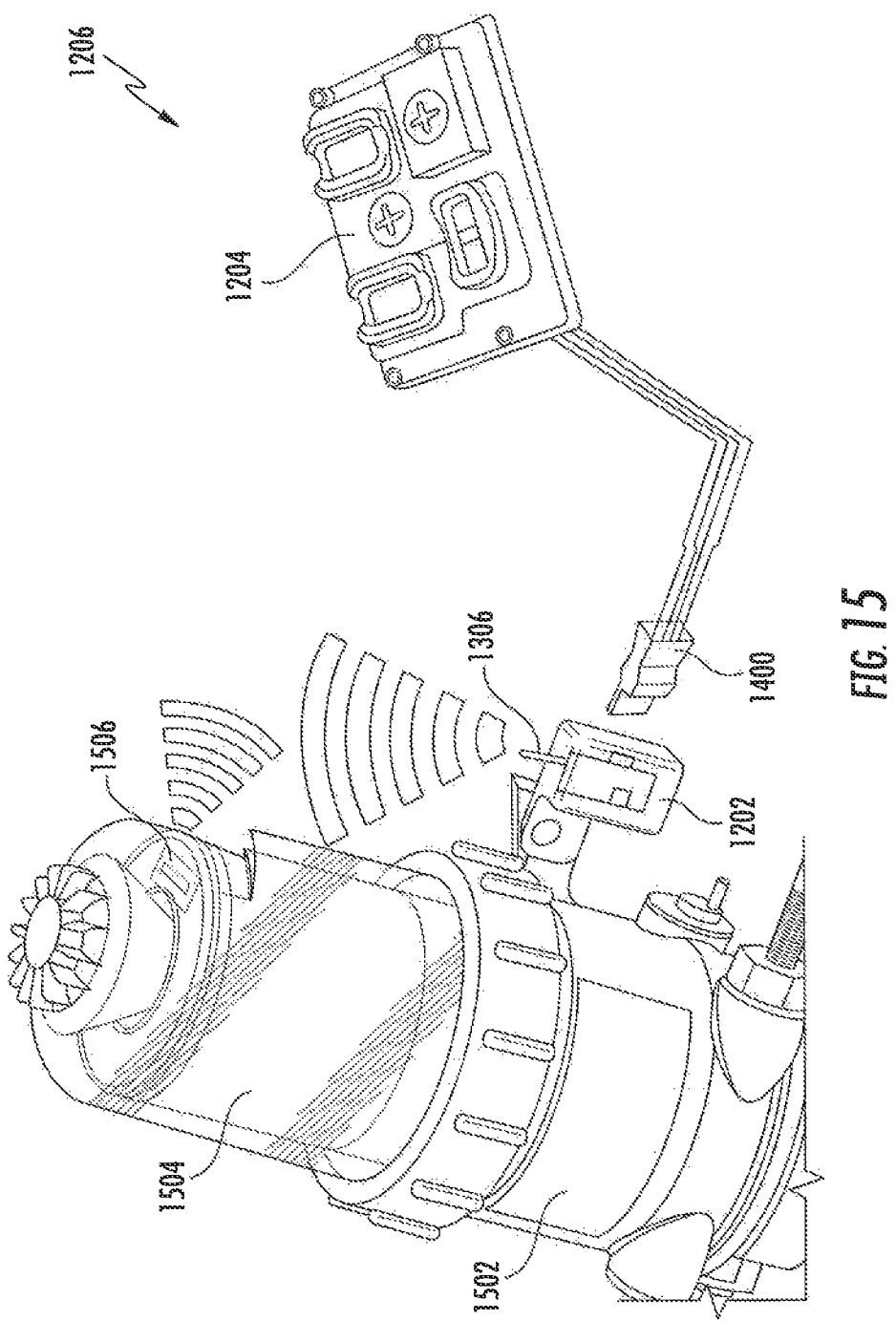
FIG. 15 is a diagram of the module of FIG. 13 installed with a filtration system.

FIG. 15 is a diagram showing the module 1202 installed with a filtration system 1502 according to an example embodiment. The filtration system 1502 includes an installed filter cartridge 1504. The installed filter cartridge includes an RFID tag 1506. In some arrangements, the RFID tag 1506 is a passive RFID tag that is embedded within the installed filter cartridge 1504 such that it is no visible to an operator or technician. The module 1202 is installed adjacent to the filtration system 1502 such that the RFID antenna 1306 is in communication range with respect to the RFID tag 1506. Accordingly, when the module 1202 receives power (e.g., at a key-on condition for the internal combustion engine), the module 1202 broadcasts an inquiry signal through the RFID antenna 1306. The inquiry signal powers the RFID tag 1506, and the RFID tag 1506 returns data stored in a memory of the RFID tag 1506 to the module 1202. Based on the returned data (e.g., based on a serial number, a filter identifier, a filter manufacturing date, a unique identifier code, etc. in the returned data), the module 1202 determines whether the installed filter cartridge 1504 is genuine or non-authorized.

Figure 16:
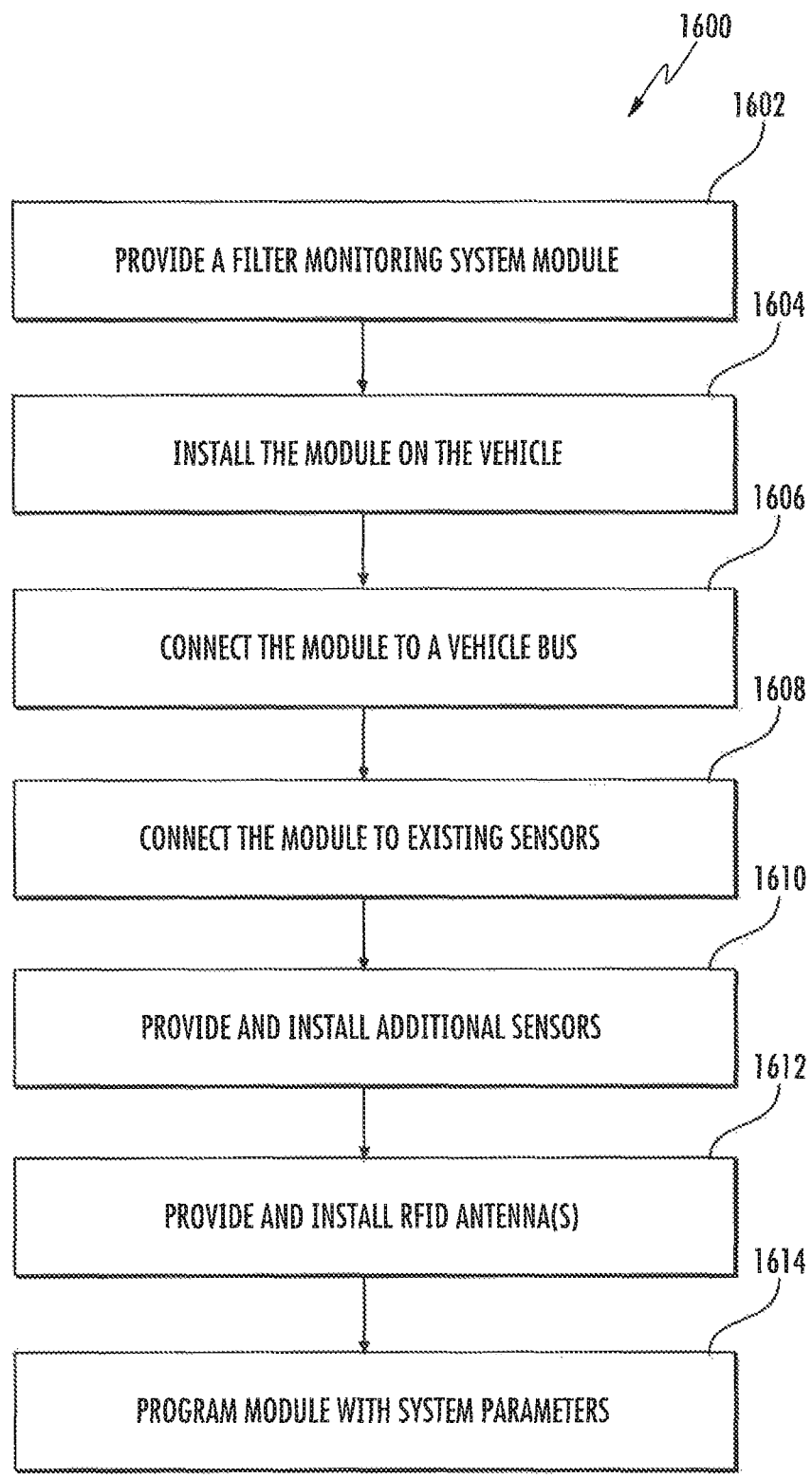
FIG. 16 is a flow diagram of a method of installing a filtration monitoring system for internal combustion engine according to an example arrangement.

Any of the above-described modules (i.e., module 102, module 902, or module 1202) can be installed on the internal combustion engine at the time of manufacture of the internal combustion engine or be installed in a retrofit manner to provided upgraded monitoring capabilities to existing internal combustion engines that do not have an existing filtration monitoring system. FIG. 16 shows a flow diagram of a method 1600 of installing a filtration monitoring system for internal combustion engine according to an example embodiment. In some arrangements, the method 1600 corresponds to retrofitting an internal combustion engine originally manufactured without a filtration monitoring system with a filtration monitoring system. The method 1600 begins when a filtration monitoring system module is provided at 1602. The filtration monitoring system module may be any of the module 102, the module 902, or the module 1202. The module is provided for installation on a vehicle powered by an internal combustion engine that does not have a filtration monitoring system.

The module is installed on the vehicle at 1604. The size of the module allows the module to be installed at various positions within the engine bay of the vehicle or adjacent to a given filtration system. In some arrangements, the module is installed by zip-tying the module to another component of the vehicle. In other arrangements, the module is installed into an existing wiring harness or socket of a vehicle bus. In such arrangements, the module may be secured into the wiring harness or socket through a screw provided on the module or on the wiring harness or socket.

The module is connected to the vehicle bus at 1606. The module is connected to the vehicle bus via a connector (e.g., the connector 700, the connector 1400, etc.) or a wiring harness. In some arrangements, the vehicle bus is a J1939 vehicle bus. The connection to the vehicle bus provides power to the module. Additionally, the connection to the vehicle bus allows the module to communicate data to and from the engine control module of the internal combustion engine. For example, connecting the module to the vehicle bus may include establishing a J1939 connection between the module and the engine control module. In some arrangements, the connection to the vehicle bus includes establishing a data connection between the module and an OE telematics box (e.g., OE telematics box 140) thereby allowing the module to communicate data to and from the OE telematics box.

Still referring to FIG. 16, existing sensors associated with the various filtration systems of the internal combustion engine are connected to the module at 1608. In some arrangements, at least some of the filtration systems of the internal combustion engine already have sensors that can provide the feedback to the module necessary for the module to compute the various filtration life calculations. In such arrangements, the existing sensors are connected via wires to the module. In other arrangements, none of the filtration systems of the internal combustion engine have the required sensors. In these arrangements, 1608 is skipped.

Additional sensors are provided and installed at 1610. If additional filtration system sensors are required, the additional sensors are provided and installed on the associated filtration systems. For example, a pressure differential may be installed on a fuel filtration system. The installed sensors (if any) are then connected to the module (e.g., via an analog data link).

In some arrangements, RFID antennas are provided and installed at 1612. The RFID antennas are positioned adjacent to the filtration systems such that the RFID antennas can interrogate RFID tags of installed filter cartridges within the filtration systems. After the RFID antennas are installed, the RFID antennas are connected to the module (e.g., via a coaxial cable).

In some arrangements, the filtration monitoring system only provides an indication as to whether a genuine filter cartridge is installed in a given filtration system (e.g., as described above with respect to the filtration monitoring system 1200). In such arrangements, 1608 and 1610 are skipped. In other arrangements, the filtration monitoring system does not provide genuine filter cartridge detection capabilities (e.g., as described above with respect to the filtration monitoring system 100). In these arrangements, 1612 is skipped.

The module is programmed with system parameters at 1614. The module is programmed such that it can monitor the filtration systems of the internal combustion engine and/or determine whether genuine filter cartridges are installed in the filtration systems of the internal combustion engine. The module is also programmed to communicate data to and from the engine control module of the internal combustion engine via the vehicle bus.

Figure 17:
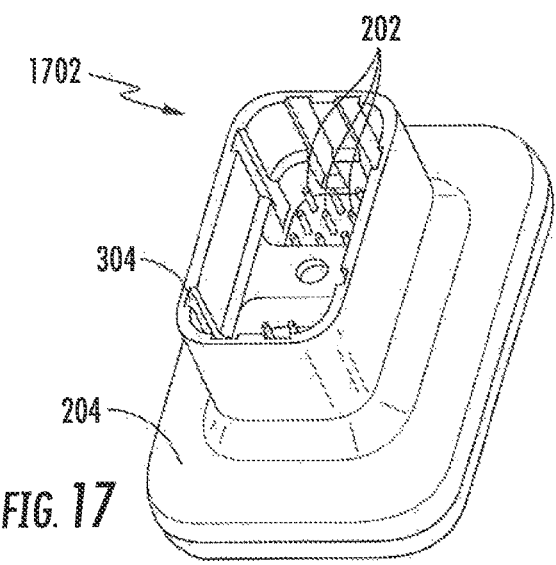
FIG. 17 is a perspective view of a module according to another example embodiment.
Figure 18:
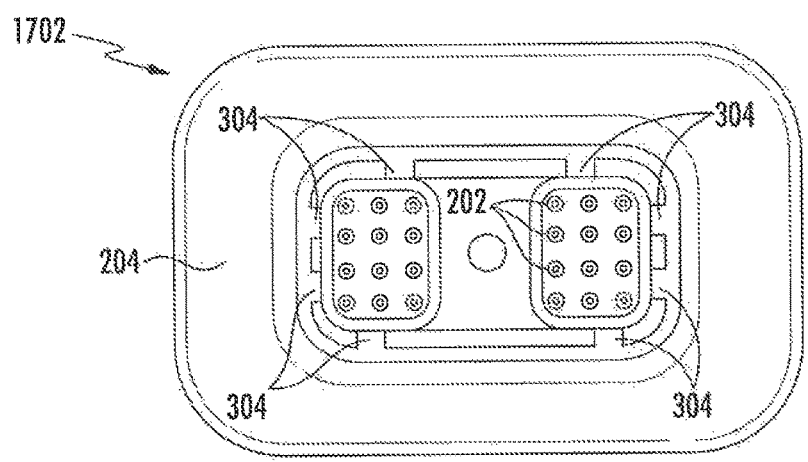
FIG. 18 is a top view of the module of FIG. 17.
Figure 19:
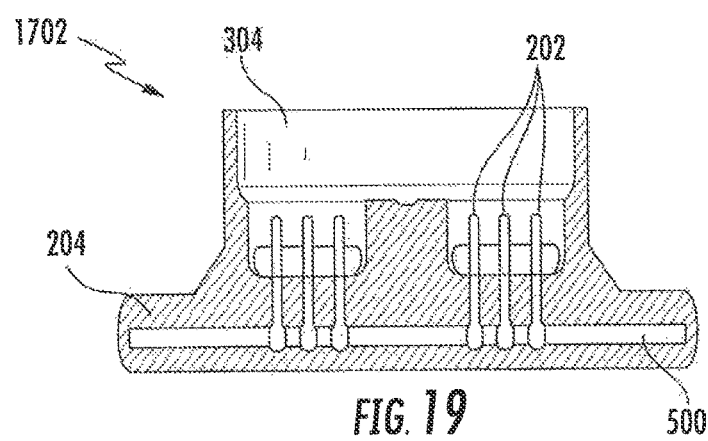
FIG. 19 is a cross-sectional side view of the module of FIG. 17.
Figure 20:
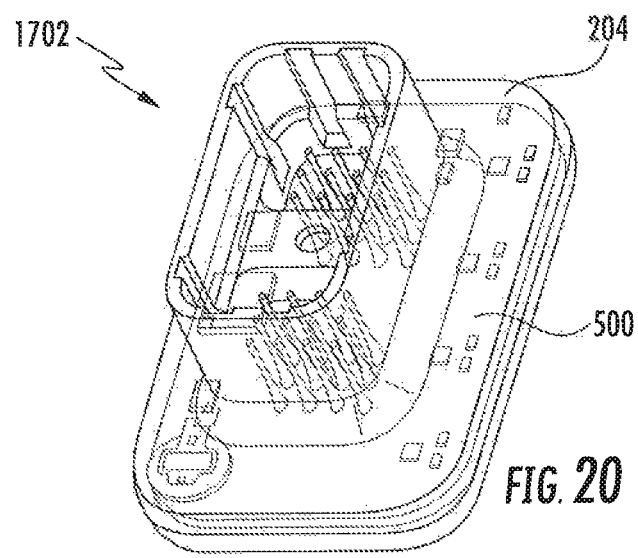
FIG. 20 is a see-through perspective view of the module of FIG. 17.
Figure 21:
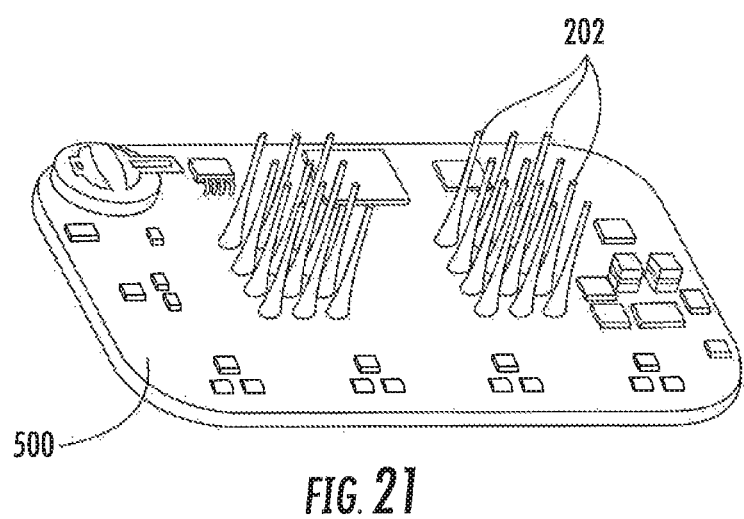
FIG. 21 is a perspective view of the circuit board of the module of FIG. 17.
Figure 22:
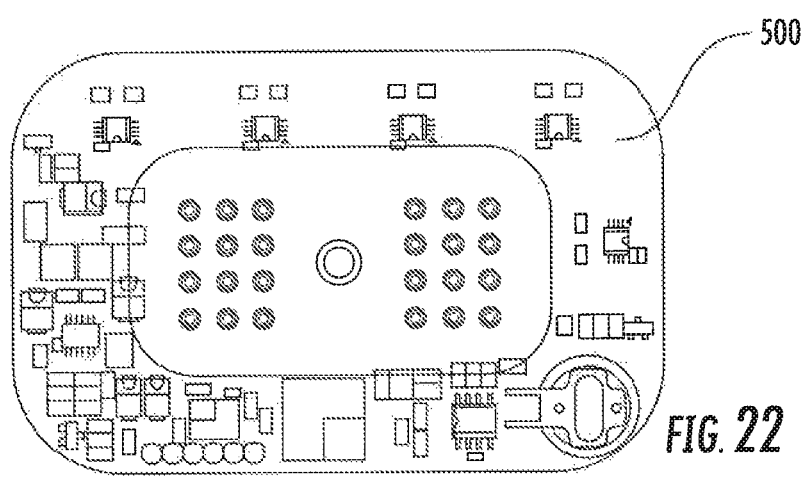
FIG. 22 is a schematic view of the circuit board of the module of FIG. 17.
Figure 23:
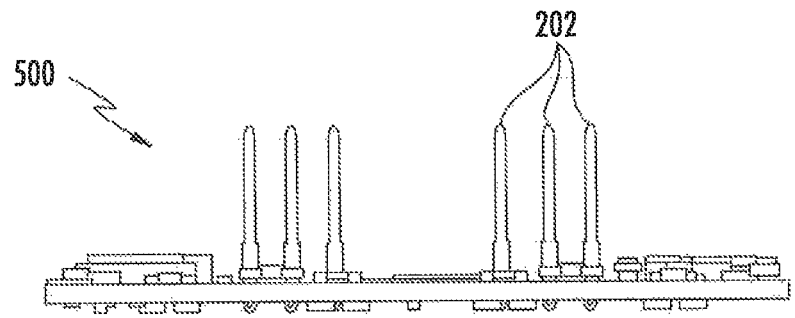
FIG. 23 is a side view of the circuit board of the module of FIG. 17.

Referring to FIGS. 17 through 23, various views of a module 1702 of a filtration monitoring system are shown according to another example embodiment. FIG. 17 shows a perspective view of the module 1702. FIG. 18 shows a top view of the module 1702. FIG. 19 shows a cross-sectional side view of the module 1702. FIG. 20 shows a see-through perspective view of the module 1702 showing the positioning of a circuit board 500 in the module 1702. FIG. 21 shows a perspective view of the circuit board 500 of the module 1702. FIG. 22 is a schematic view of the circuit board 500. FIG. 23 is a side view of the circuit board 500.

The module 1702 is similar in form and function with the module 102. As described in further detail below, a primary difference between the module 102 and the module 1702 is the arrangement of the pins 202 of the module 1702. Accordingly, the same numbering is used between the module 1702 and the module 102 to designate similar parts. As shown best in FIGS. 17, 18, 20, and 21, the module 1702 includes twenty-four pins 202 (unlike the module 102, which includes fifty pins 202). In some arrangements, the pins 202 of the module 1702 are arranged in two three by four arrays (e.g., as shown in FIG. 18). In other arrangements, the pins may be arranged in a single array, a plurality of rows, a random pattern across the surface of the circuit board 500, or in still other arrangements.

Figure 24:
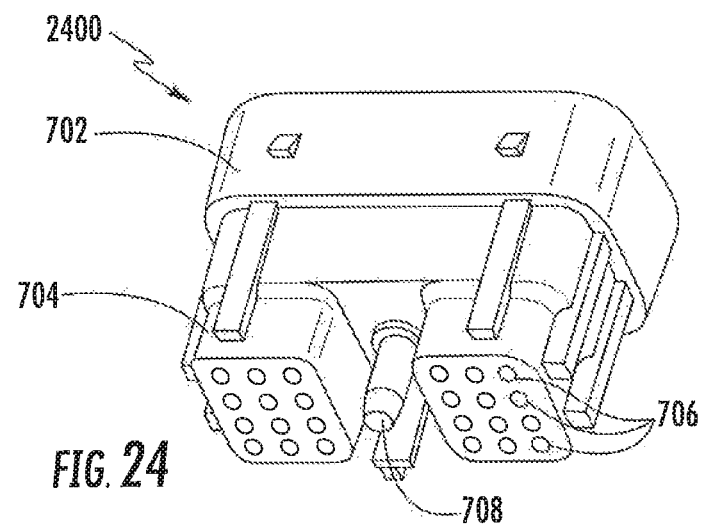
FIG. 24 shows a perspective view of a connector for the module of FIG. 17 according to an example embodiment.
Figure 25:
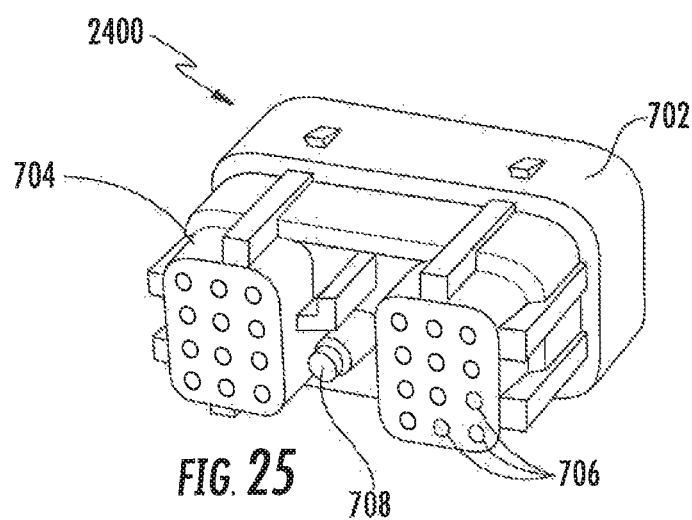
FIG. 25 shows another perspective view of the connector of FIG. 24.

Referring to FIGS. 24 and 25, two perspective views of a connector 2400 are shown according to an example embodiment. The connector 2400 is similar in design and function to the connector 700. Accordingly, like numbering is used to designate like parts between the connector 2400 and the connector 700. The primary difference between the connector 2400 and the connector 700 is that the connector 2400 is structured to connect with the module 1702, and the connector 700 is structured to connect with the module 102. Accordingly, the connector 2400 has a different arrangement of pin connectors 706 than the connector 700. The pin connectors 706 of the connector 2400 are arranged in two three by four arrays to properly align with and receive the pins 202 of the module 1702.

The above-described filtration monitoring systems are applicable to different types of internal combustion engines (e.g., diesel internal combustion engines, high horsepower internal combustion engines, etc.) and vehicles or equipment powered by internal combustion engines (e.g., mining equipment). The filtration monitoring systems provide real-time filtration system information (e.g., percentage loading of filters, oil quality information, remaining service life of filter cartridge information, etc.) using the real-time feedback form the various sensors and the engine control module parameters. This information allows operators of the internal combustion engines to reduce total cost of ownership by eliminating planned and unplanned maintenance events thereby reducing downtime of the equipment. For example, based on the feedback from the filtration monitoring systems 100 and 900, technicians can proactively predict the remaining service life of given filter cartridges to better manage scheduling of service intervals to synchronize the filter services to reduce overall downtime of the equipment. Accordingly, filtration system maintenance can be shifted from a fixed schedule to a flexible condition based maintenance schedule by synchronizing filtration system service events (e.g., by synchronizing when the fuel filter cartridge, air filter cartridge, etc. are replaced), which allows for better management and more efficient scheduling of service intervals on fleet vehicles. Doing so additionally extends and optimizes the useful service life of the filtration systems, increases fuel economy by ensuring properly maintained filtration systems, and reduces warranty claims and failure by ensuring the filtration systems are properly maintained.

It should be noted that the terms "example" as used herein to describe various embodiments are intended to indicate that such embodiments are possible examples, representations, and/or illustrations of possible embodiments (and such term is not intended to connote that such embodiments are necessarily extraordinary or superlative examples).

The terms "connected" and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another.

References herein to the positions of elements (e.g., "top," "bottom," "above," "below," etc.) are merely used to describe the orientation of various elements in the figures. It should be noted that the orientation of various elements may differ according to other exemplary embodiments, and that such variations are intended to be encompassed by the present disclosure.

It is important to note that the construction and arrangement of the various exemplary embodiments are illustrative only. Although only a few embodiments have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. For example, elements shown as integrally formed may be constructed of multiple parts or elements, the position of elements may be reversed or otherwise varied, and the nature or number of discrete elements or positions may be altered or varied. The order or sequence of any process or method steps may be varied or re-sequenced according to alternative embodiments. Other substitutions, modifications, changes and omissions may also be made in the design, operating conditions and arrangement of the various exemplary embodiments without departing from the scope of the present invention.

Many of the functional units described in this specification have been labeled as circuits, in order to more particularly emphasize their implementation independence. For example, a circuit may be implemented as a hardware circuit comprising custom very-large-scale integration (VLSI) circuits or gate arrays, off-the-shelf semiconductors such as logic chips, transistors, or other discrete components. A circuit may also be implemented in programmable hardware devices such as field programmable gate arrays, programmable array logic, programmable logic devices or the like.

As mentioned above, circuits may also be implemented in machine-readable medium for execution by various types of processors, such as the processor of the module 102. An identified circuit of executable code may, for instance, comprise one or more physical or logical blocks of computer instructions, which may, for instance, be organized as an object, procedure, or function. Nevertheless, the executables of an identified circuit need not be physically located together, but may comprise disparate instructions stored in different locations which, when joined logically together, comprise the circuit and achieve the stated purpose for the circuit. Indeed, a circuit of computer readable program code may be a single instruction, or many instructions, and may even be distributed over several different code segments, among different programs, and across several memory devices. Similarly, operational data may be identified and illustrated herein within circuits, and may be embodied in any suitable form and organized within any suitable type of data structure. The operational data may be collected as a single data set, or may be distributed over different locations including over different storage devices, and may exist, at least partially, merely as electronic signals on a system or network.

The computer readable medium (also referred to herein as machine-readable media or machine-readable content) may be a tangible computer readable storage medium storing computer readable program code. The computer readable storage medium may be, for example, but not limited to, an electronic, magnetic, optical, electromagnetic, infrared, holographic, micromechanical, or semiconductor system, apparatus, or device, or any suitable combination of the foregoing. As alluded to above, examples of the computer readable storage medium may include but are not limited to a portable computer diskette, a hard disk, a random access memory (RAM), a read-only memory (ROM), an erasable programmable read-only memory (EPROM or Flash memory), a portable compact disc read-only memory (CD-ROM), a digital versatile disc (DVD), an optical storage device, a magnetic storage device, a holographic storage medium, a micromechanical storage device, or any suitable combination of the foregoing. In the context of this document, a computer readable storage medium may be any tangible medium that can contain, and/or store computer readable program code for use by and/or in connection with an instruction execution system, apparatus, or device.

The computer readable medium may also be a computer readable signal medium. A computer readable signal medium may include a propagated data signal with computer readable program code embodied therein, for example, in baseband or as part of a carrier wave. Such a propagated signal may take any of a variety of forms, including, but not limited to, electrical, electro-magnetic, magnetic, optical, or any suitable combination thereof. A computer readable signal medium may be any computer readable medium that is not a computer readable storage medium and that can communicate, propagate, or transport computer readable program code for use by or in connection with an instruction execution system, apparatus, or device. As also alluded to above, computer readable program code embodied on a computer readable signal medium may be transmitted using any appropriate medium, including but not limited to wireless, wireline, optical fiber cable, Radio Frequency (RF), or the like, or any suitable combination of the foregoing. In one embodiment, the computer readable medium may comprise a combination of one or more computer readable storage mediums and one or more computer readable signal mediums. For example, computer readable program code may be both propagated as an electro-magnetic signal through a fiber optic cable for execution by a processor and stored on RAM storage device for execution by the processor.

Computer readable program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The computer readable program code may execute entirely on the user's computer (such as via the module 102 of FIGS. 1-8), partly on the user's computer, as a stand-alone computer-readable package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). The program code may also be stored in a computer readable medium that can direct a computer, other programmable data processing apparatus, or other devices to function in a particular manner, such that the instructions stored in the computer readable medium produce an article of manufacture including instructions which implement the function/act specified in the schematic flowchart diagrams and/or schematic block diagrams block or blocks.

Accordingly, the present disclosure may be embodied in other specific forms without departing from its spirit or essential characteristics. The described embodiments are to be considered in all respects only as illustrative and not restrictive. The scope of the disclosure is, therefore, indicated by the appended claims rather than by the foregoing description. All changes which come within the meaning and range of equivalency of the claims are to be embraced within their scope.

What is claimed is:

1. An apparatus, comprising:
   an internal combustion engine having an engine control module structured to control the operation of the internal combustion engine;
   an air filtration system having a first filter cartridge;
   a fluid filtration system having a second filter cartridge
   a first pressure sensor structured to sense a characteristic associated with the air filtration system;
   a second pressure sensor structured to sense a characteristic associated with the fluid filtration system;
   a filtration monitoring system module including a processing circuit communicatively coupled to the sensor, the processing circuit including a processor and memory, the processing circuit structured to:
   receive a feedback signal from each of the first pressure sensor relating to the characteristic associated with the air filtration system and the second pressure sensor related to the characteristic associated with the fluid filtration system,
   analyze the feedback signals to determine a status of each of the first filter cartridge and the second filter cartridge,
   calculate a percent loading of each of the first filter cartridge and the second filter cartridge, and
   transmit each of the percent loading of the filter cartridges to the engine control module; and
   wherein the engine control module is structured to transmit, via a telematics system, batch data comprising the status and the percent loading of each of the first filter cartridge and the second filter cartridge.

2. The apparatus of claim 1, wherein the engine control module is communicatively coupled to the filtration monitoring system module through a digital data link, the engine control module structured to provide real-time operating parameters of the internal combustion engine to the filtration monitoring system module.

3. The apparatus of claim 2, wherein the processing circuit is structured to provide status information of the air filtration system and the fluid filtration system to the engine control module.

4. The apparatus of claim 1, wherein the filtration monitoring system module includes at least seven analog input channels, and wherein each sensor is communicatively coupled to one of the at least seven analog input channels.

5. The apparatus of claim 4, wherein the filtration monitoring system module includes ten analog input channels.

6. The apparatus of claim 4, wherein the filtration monitoring system module includes an analog to digital converter circuit structured to convert the respective feedback signal from the first pressure sensor from an analog signal to a digital signal prior to analyzing the respective feedback signal.

7. The apparatus of claim 1, further comprising a radio frequency antenna communicatively coupled to the filtration monitoring system module and structured to interrogate and gather data from a radio frequency identifier tag installed on the first filter cartridge and to send the data to the filtration monitoring system module, wherein the data includes a unique identifier of the first filter cartridge.

8. The apparatus of claim 7, wherein the processing circuit is further structured to determine whether the first filter cartridge is a genuine filter cartridge based on the unique identifier.

9. The apparatus of claim 1, further comprising:
   a lubrication filtration system having a third filter cartridge
   a third pressure sensor structured to sense a second characteristic associated with the fluid filtration system, wherein the second pressure sensor is associated with a first stage of the fluid filtration system, and the third pressure sensor is associated with a second stage of the fluid filtration system;
   a fourth pressure sensor structured to sense a characteristic associated with the lubrication filtration system;
   wherein the processing circuit of the filtration monitoring system module is further structured to:
   receive a feedback signal from each of the third pressure sensor and the fourth pressure sensor, analyze the feedback signals of each of the third pressure sensor and the fourth pressure sensor to determine the status of each of the second filter cartridge and the third filter cartridge, calculate a percent loading of the third filter cartridge, transmit the percent loading of the third filter cartridge to the engine control module; and wherein the batch data further comprises the status and the percent loading of the third filter cartridge.

10. A method of installing a filtration monitoring system for an internal combustion engine, the method comprising:

providing a filtration monitoring system module having a processing circuit structured to:

receive a first feedback signal from a first pressure sensor associated with an air filtration system associated with the internal combustion engine, analyze the first feedback signal to determine a status of a first filter cartridge of the air filtration system, and calculate a percent loading of the first filter cartridge, and receive a second feedback signal from a second pressure sensor associated with a fluid filtration system associated with the internal combustion engine, analyze the second feedback signal to determine a status of a second filter cartridge of the fluid filtration system, and calculate a percent loading of the second filter cartridge;

connecting the filtration monitoring system module to the first pressure sensor and to the second pressure sensor;

providing an engine control module having a processing circuit structured to transmit, via a telematics system, batch data comprising the status and percent loading of the first filter cartridge and the status and percent loading of the second filter cartridge; and connecting the filtration monitoring system module to a vehicle bus such that the filtration monitoring system module can communicate data to and from an engine control module of the internal combustion engine.

11. The method of claim 10, wherein the installing of the filtration monitoring system comprises retrofitting the internal combustion engine that was originally manufactured without an original filtration monitoring system.

12. The method of claim 10, further comprising:

providing a radio frequency identification antenna structured to interrogate a radio frequency identification tag of the first filter cartridge of the air filtration system; and connecting the radio frequency identification antenna to the filtration monitoring system module.

13. The method of claim 10, wherein connecting the filtration monitoring system module to a vehicle bus includes establishing a J1939 data connection between the filtration monitoring system module and the engine control module.

14. The method of claim 10, further comprising establishing a data connection between the engine control module and a telematics box.

15. The method of claim 10, wherein the processing circuit of the filtration monitoring system module is further structured to:

receive a third feedback signal from a third pressure sensor associated with a lubrication filtration system associated with the internal combustion engine, analyze the third feedback signal to determine a status of a third filter cartridge of the lubrication filtration system, and calculate a percent loading of the third filter cartridge; and wherein the batch data further comprises the status and percent loading of the third filter cartridge.

\* \* \* \* \*